(12) United States Patent
Morales

(10) Patent No.: US 11,806,523 B2
(45) Date of Patent: Nov. 7, 2023

(54) TRANSCATHETER ELECTRODE ARRAY AND USE THEREOF

(71) Applicant: JUAD, INC., Oceanside, CA (US)

(72) Inventor: Jose Miguel Morales, Los Angeles, CA (US)

(73) Assignee: VONOVA INC., Oceanside, CA (US)

( * ) Notice: Subject to any disclaimer, the term of this patent is extended or adjusted under 35 U.S.C. 154(b) by 0 days.

(21) Appl. No.: 18/013,829

(22) PCT Filed: Jun. 30, 2021

(86) PCT No.: PCT/US2021/039962
§ 371 (c)(1),
(2) Date: Dec. 29, 2022

(87) PCT Pub. No.: WO2022/006317
PCT Pub. Date: Jan. 6, 2022

(65) Prior Publication Data
US 2023/0191117 A1    Jun. 22, 2023

Related U.S. Application Data

(63) Continuation-in-part of application No. PCT/US2020/041246, filed on Jul. 8, 2020.

(60) Provisional application No. 63/045,984, filed on Jun. 30, 2020.

(51) Int. Cl.
*A61N 1/18* (2006.01)
*A61N 1/05* (2006.01)

(52) U.S. Cl.
CPC ............. *A61N 1/0534* (2013.01); *A61N 1/18* (2013.01)

(58) Field of Classification Search
CPC ............................... A61N 1/0534; A61N 1/18
See application file for complete search history.

(56) References Cited

U.S. PATENT DOCUMENTS

| 6,068,638 | A  | 5/2000  | Makower        |
| 6,190,353 | B1 | 2/2001  | Makower et al. |
| 6,217,527 | B1 | 4/2001  | Selmon et al.  |
| 6,491,707 | B2 | 12/2002 | Makower et al. |

(Continued)

FOREIGN PATENT DOCUMENTS

| WO | WO2016/131020 A1 | 8/2016 |
| WO | WO2021/007346 A1 | 1/2021 |
| WO | WO2021/097448 A1 | 5/2021 |

OTHER PUBLICATIONS

Search Report and Written Opinion issued in International Application No. PCT/US2021/039962, dated Oct. 19, 2021 (7 pages).

(Continued)

*Primary Examiner* — Ankit D Tejani
*Assistant Examiner* — Joshua Brendon Solomon
(74) *Attorney, Agent, or Firm* — BLAIR WALKER IP SERVICES, LLC

(57) ABSTRACT

The present disclosure is directed towards devices, methods, and related systems that are minutely-invasively delivered to the brain parenchyma, subdural or subarachnoid space where the devices, methods, and systems directly interface with central nervous system media (i.e., fluid or tissue) enabling detecting, sensing, measuring, stimulating, altering and/or modulating of the media or tissue surfaces.

20 Claims, 13 Drawing Sheets

(56) References Cited

U.S. PATENT DOCUMENTS

| | | |
|---|---|---|
| 6,511,458 B2 | 1/2003 | Milo et al. |
| 6,544,230 B1 | 4/2003 | Flaherty et al. |
| 6,660,024 B1 | 12/2003 | Flaherty et al. |
| 6,669,687 B1 | 12/2003 | Saadat |
| 6,685,716 B1 | 2/2004 | Flaherty et al. |
| 6,692,466 B1 | 2/2004 | Chow et al. |
| 6,694,983 B2 | 2/2004 | Wolf et al. |
| 6,709,444 B2 | 3/2004 | Makower |
| 6,726,677 B1 | 4/2004 | Flaherty et al. |
| 7,141,041 B2 | 11/2006 | Seward |
| 7,273,469 B1 | 9/2007 | Chan et al. |
| 8,483,794 B2 | 7/2013 | Williams et al. |
| 8,543,223 B2 | 9/2013 | Sage et al. |
| 8,636,715 B2 | 1/2014 | Patel |
| 8,721,590 B2 | 5/2014 | Seward et al. |
| 8,753,366 B2 | 6/2014 | Makower et al. |
| 8,805,466 B2 | 8/2014 | Salahieh et al. |
| 9,220,874 B2 | 12/2015 | Pillai et al. |
| 9,289,141 B2 | 3/2016 | Lowery et al. |
| 9,511,214 B2 | 12/2016 | Pillai |
| 9,877,833 B1 | 1/2018 | Bishop et al. |
| 10,124,195 B2 | 11/2018 | Zarins et al. |
| 10,166,385 B2 | 1/2019 | Bedenbaugh |
| 10,485,968 B2 | 11/2019 | Opie et al. |
| 11,013,900 B2 | 5/2021 | Malek et al. |
| 2002/0002349 A1 | 1/2002 | Flaherty et al. |
| 2004/0243204 A1* | 12/2004 | Maghribi ............ A61N 1/0551 607/115 |
| 2005/0137647 A1* | 6/2005 | Wallace ............... A61N 1/0531 607/45 |
| 2009/0142306 A1 | 6/2009 | Seward et al. |
| 2009/0222083 A1 | 9/2009 | Nguyen et al. |
| 2010/0185172 A1 | 7/2010 | Fabro |
| 2010/0198297 A1* | 8/2010 | Cogan .................... A61N 1/025 607/45 |
| 2010/0211131 A1 | 8/2010 | Williams et al. |
| 2010/0249491 A1 | 9/2010 | Farnan et al. |
| 2012/0053485 A1 | 3/2012 | Bloom |
| 2012/0136247 A1 | 5/2012 | Pillai |
| 2013/0103026 A1 | 4/2013 | Kleshinski et al. |
| 2013/0245430 A1 | 9/2013 | Selmon et al. |
| 2013/0245533 A1 | 9/2013 | Kahn et al. |
| 2014/0121749 A1 | 5/2014 | Roeder |
| 2014/0378906 A1 | 12/2014 | Fischell et al. |
| 2015/0141836 A1 | 5/2015 | Naumann et al. |
| 2016/0001060 A1* | 1/2016 | Black ................... A61N 1/0558 607/116 |
| 2016/0193459 A1 | 7/2016 | Gaudiani |
| 2016/0374710 A1 | 12/2016 | Sinelnikov et al. |
| 2017/0157375 A1 | 6/2017 | Heilman |
| 2017/0231563 A1 | 8/2017 | Tsamir et al. |
| 2017/0231572 A1 | 8/2017 | Lowery |
| 2017/0246427 A1 | 8/2017 | Gurley |
| 2018/0161550 A1 | 6/2018 | Pillai et al. |
| 2018/0161551 A1 | 6/2018 | Pillai |
| 2018/0289949 A1 | 10/2018 | Bachinski et al. |
| 2019/0008580 A1 | 1/2019 | Fischell et al. |
| 2019/0038438 A1* | 2/2019 | John ........................ A61F 2/68 |
| 2019/0134349 A1 | 5/2019 | Cohn et al. |
| 2019/0105477 A1 | 6/2019 | Heilman et al. |
| 2020/0375766 A1 | 12/2020 | Malek |
| 2021/0046305 A1 | 2/2021 | Rosa et al. |
| 2021/0213279 A1 | 7/2021 | Rapoport et al. |
| 2021/0361950 A1 | 11/2021 | Opie et al. |
| 2021/0373665 A1 | 12/2021 | Yoo |
| 2021/0378595 A1 | 12/2021 | Oxley |
| 2022/0033952 A1 | 2/2022 | Diaz-Botia |
| 2022/0241596 A1 | 8/2022 | Opie et al. |
| 2022/0253024 A1 | 8/2022 | Oxley et al. |
| 2022/0369994 A1 | 11/2022 | Oxley |

OTHER PUBLICATIONS

"Ultrathin needle can deliver drugs directly to the brain" MIT News, https://news.mit.edu/2018/ultrathin-needle-can-deliver-drugs-directly-brain-0124 dated Jan. 24, 2018 (6 pages).

Dhanasingh A, Jolly C, "An overview of cochlear implant electrode array designs," Hearing Research (2017) 356:93-103 www.elsevier.com/locate/heares.

* cited by examiner

TRANSCATHETER ELECTRODE ARRAY AND USE THEREOF

CROSS-REFERENCE TO RELATED APPLICATIONS

This application is a continuation-in-part of PCT Application PCT/US2020/041246 filed Jul. 8, 2020, and also claims the benefit of U.S. Provisional Patent Application No. 63/045,984, filed Jun. 30, 2020, both of which are explicitly incorporated herein in their entirety by reference.

TECHNICAL FIELD

The present disclosure relates to a device implantable or deliverable across the wall of a blood vessel for sensing, stimulating, and/or modulating central nervous system media (i.e., tissue or fluid), and related systems and methods for utilizing the blood vessels as a conduit to access media or tissue in extravascular spaces. More particularly, this disclosure relates to an implantable medical device introduced across the wall of a blood vessel within the intracranial vault deployed from a flexible hollow instrument for the purpose of directly interfacing with regions of the brain exhibiting normal or abnormal neurophysiologic activity.

BACKGROUND OF THE INVENTION

There is a secular trend in chronic disease prevalence driven by a global aging population and improvements in imaging technology and detection methods that enable earlier diagnosis. Likewise, the incidence of neurologic disease continues to rise worldwide as well as the demand for more precise and less invasive methods of diagnosis and treatment due to increasing global awareness. Minimally invasive catheter-based approaches to medical intervention are experiencing rising demand due to preference by clinicians and patients alike, and recognition by payers of the potential cost-savings to the healthcare system.

Neuroendovascular treatments of aneurysms and arteriovenous malformations have progressively comprised a larger share of treated patients around the world and are now the preferred method of treatment in a majority of cases. From a healthcare systems perspective, minimally invasive surgeries and procedures have been associated with the early adoption of novel diagnostic or therapeutic devices or materials, a lower threshold to treat, a reduction in hospitalization costs, improved patient comfort, and a decrease in perioperative complications.

In the US, nearly 5.4 million people live with paralysis while 70 million people worldwide are affected by epilepsy. Paralysis patients would benefit from a minimally invasive direct neural interface in that the interface may enable communication, operate a robotic limb (s), or control/manipulate devices or computer interfaces. Focal recurrent seizures accounts for approximately 60% of epilepsy cases, and as many as 40% of focal epilepsy patients may progress to pharmaco-refractoriness. Many pharmaco-resistant focal epilepsy patients should undergo invasive mapping and may require surgery to achieve effective seizure control. Pharmacoresistant epilepsy not only severely impacts the lives of a significant portion of affected patients but is also life threatening. Medically refractory epilepsy is a progressive disease associated with significant morbidity and premature death. Evidence suggests early surgical intervention improves seizure outcomes and quality of life for patients with refractory focal epilepsy. However, open and stereotactic neurosurgery are highly invasive surgical procedures requiring scalp incision, burr holes, and, often include collateral brain tissue damage. Despite evidence of its efficacy and tolerable surgical risk profile, many physicians are reluctant to recommend surgery owing to perceptions of its riskiness and invasiveness. Additionally, elective neurosurgery provokes significant fear and anxiety in patients leading to morbidity tolerance and underutilization of neurosurgical treatments.

The symptoms of specific neurologic or psychiatric diseases/disorders may be attributable to abnormal cortical network activity and may be treated by the disruption or modulation of abnormal cortical single unit or network activity. Specific examples include hyper-synchronization of cortico-striatal networks in Parkinson's disease and essential tremor. Aberrant activity of cortico-striatal and thalamocortical loops in neuropsychiatric disorders (Obsessive Compulsive Disorder (OCD), Major Depressive Disorder, Tourette's Syndrome, Schizophrenia, Generalized Anxiety Disorder, Pain, Addiction and the like) may be refractory to pharmacologic or other non-invasive treatments. For instance, OCD affects approximately 2.2 million people in the US and as many as 40% are refractory to medical management. Another example is major depressive disorder, which affects nearly 21 million adults in the US of which nearly 30% are pharmacoresistant.

Plasticity-inducing, modulatory, and neuroregenerative electroceutical neuroprosthetic devices may serve to improve function in cognitive, motor, and behavioral impairments associated with brain injury and degenerative diseases (traumatic brain injury, Alzheimer's disease, Pick's disease, Primary Progressive Aphasia, Parkinson's disease, Corticobasal Degeneration, Primary Lateral Sclerosis, Amyotrophic Lateral Sclerosis, Demyelinating Disease, and the like).

In many of these neurologic conditions, the perceived harm-to-benefit ratio of invasive diagnostics and therapeutics impacts the threshold to appropriate and timely treatment, and delays in definitive therapy may adversely impact long-term outcomes. A less invasive method of accessing the brain has the potential to lower the threshold for early intervention and by extension improve long-term outcomes for a many neurologic diseases and disorders. Since their inception percutaneous catheter-based methods have lowered the threshold and broadened the inclusion criteria for diagnosing and treating disease earlier in its course or in patients with advanced or co-morbid disease otherwise deemed too high risk for standard surgical approaches. A method for accessing the cortex that does not require burr holes or craniotomy is advantageous and may serve to expand the clinical indication for sensing, stimulating, modulating, altering, or communicating with tissue or media of the central nervous system, as well as serve as a modality for the augmentation or expansion of cognitive abilities in otherwise healthy subjects. A less invasive method has the potential to expedite clinically indicated treatment, which may improve quality of life and outcomes, as well as decrease length of stays and healthcare related costs.

Current methods for recording, stimulating, modulating, or decoding signals arising from the cortical brain tissue utilize electrode array or linear probe devices in clinical applications. Electrocorticography arrays provide large spatial coverage of the cortical surface. Current methods for implanting electrode arrays, probes, strips, devices, or leads require craniotomy or burr hole, which are highly invasive surgeries that expose patients to the risk of bleeding, infection, and disabling neurological deficits, as well as post-operative pain and cosmetic disfigurement. Moreover, many of these surgical procedures require anesthesia and prolonged operative times exposing the patient to risks beyond the surgery itself.

Current minimally invasive systems, such as stereotactic neurosurgical methods, are constrained by their reliance of rigid or semi-rigid instruments (i.e., endoscopes), linear line-of-sight trajectories, blind advancement or use static or temporally irresolute images and/or external fiducial markers, and are associated with excess collateral damage to normal or non-disease brain tissue en-route to its intended target. The medical device disclosed herein is suitable for implantation on the surface of the brain (i.e., grey matter) located within or in close proximity to the subarachnoid, or more preferably the subdural space. The device is delivered to the surface of the brain using flexible/semi-flexible catheters, endoscopes, cannulas, or needles that have crossed the vessel wall of an animal to a space where media or tissue is located within the intracranial vault.

Invasive neurosurgery may be the most effective treatment for many of these neurological disorders yet remains underutilized in large part due to its perceived riskiness and invasiveness, as well as its costs and prolonged recovery time. Despite advances in materials science, microengineering, miniaturized and wireless technology, methods for accessing the brain with minimally invasive, catheter-based approaches remain underdeveloped for neurological diseases and disorders. Directly accessing tissue or media within the intracranial vault without burr holes or craniotomy represents a significant breakthrough in basic, translational, and clinical neuroscience. Therefore, a minimally invasive non-surgical approach to accessing the brain without burr holes or craniotomy has the potential to lower the harm-to-benefit ratio, promote early intervention, and improve overall outcomes in neurological disorders, as well as to reduce costs.

SUMMARY OF THE DISCLOSURE

It is against the above background that the present disclosure provides certain advantages and advancements over the prior art.

Although the disclosure described herein is not limited to specific advantages or functionalities, the disclosure provides a device for detecting, sensing, measuring, recording, stimulating, modulating, altering, and/or communicating with media (i.e., tissue or fluid) at the site of device implantation in the central nervous system, wherein the intracranial implant comprises: (a) an array having one or more substrate members compressible and/or deliverable within a lumen of a flexible hollow delivery instrument to enable its delivery via an endovascular route and expandable intracranially once deployed from said instrument to occupy a volume or area via microactuating or self-actuating properties in an extravascular neuroanatomical region of interest; (b) one or more substrate members embedded with electrodes having a cortical facing or neural interfacing side; (c) electrically conductive wiring coupled to the electrodes and extending along an insertion shaft; (d) and a control device configured to electrically couple the implantable device to an external device for acquiring, processing, amplifying, or transmitting detected neurophysiologic signals.

One embodiment of the disclosure is directed to a transvenous, transdural, or transarterial intracranial electrode intracranial electrode array device wherein the device implantation occurs by way of introducing the array intravascularly in a compressed state within the confines of a flexible hollow delivery instrument; subsequent extravascular deployment of the electrode array device out of the flexible hollow delivery instrument introduced through a transvascular access site configured for extravascular advancement or navigation within the intracranial vault, comprising a neural interfacing array delivered via a transvascular procedure catheter dimensioned to be launched out of the side exit port by the selective deflector configured to deliver the array in the intracranial subdural or subarachnoid space for direct contact with the tissue or media; and interfacing with a large spatial area of media or tissue due to expanding dimensions within the space.

One embodiment of the disclosure is directed to a transvenous, transdural, or transarterial intracranial electrode electrode array device, comprised of a substrate embedded with conductive materials, which is collapsible, crimpable, compressible, or houseable within the confines of a flexible hollow delivery instrument, as well as expandable in a planar and/or a conformable configuration, which directly overlay the topography of the media or tissue of the central nervous system.

One embodiment of the disclosure is directed to a transvenous, transdural, or transarterial intracranial electrode array device wherein a plurality of elongate members comprised of flexible thin-film materials with intrinsic (i.e., shape memory materials/alloys or hydroabsorbant materials) or extrinsic (i.e., microfluidic hydraulic channels) microactuating properties expand the device in a 2 or 3 dimensional plane parallel to the topography of the cortical surface.

One embodiment of the disclosure is directed to a transvenous, transdural, or transarterial intracranial electrode array device comprising a plurality of elongate thin-film substrate members together forming a scaffold forming an array embedded with electrodes, wherein two of the elongate thin-film substrate members are such that the two members are movable relative to one another; wherein the array comprises a plurality of individual elongate members; wherein the individual elongate members uniformly expand in one plane allowing the thin-film substrate members forming the array to increase spatial coverage in at least 1 or more preferably 2 to 3 dimensions.

One embodiment of the disclosure is directed to a transvenous, transdural, or transarterial intracranial electrode array device further comprising a plurality of interconnected members, wherein two of the interconnected segments are interconnected such that the two or more members are movable relative to one another for a reduced profile; wherein the coupler comprises a plurality of interconnected segments disposed between the two segments; and a portion of the individual pleats expand or contract, allowing the housing to bend.

One embodiment of the disclosure is directed to a transvenous, transdural, or transarterial intracranial electrode array device wherein the scaffold contacts a medium or tissue in a plane parallel to the cortical surface.

One embodiment of the disclosure is directed to a transvenous, transdural, or transarterial intracranial electrode array device comprising an electrode housing scaffold wherein the electrode supporting scaffold or framework comprises materials suitable for actuation and which provide the electrode supporting scaffold or framework with enough tensile strength, such that the array does not buckle when deployed from a hollow delivery instrument; and so that the array reaches the entire extent of its intended length.

One embodiment of the disclosure is directed to a transvenous, transdural, or transarterial intracranial electrode array device wherein the electrodes size is between about 20 microns to about 1.5 mm in diameter.

One embodiment of the disclosure is directed to a transvenous, transdural, or transarterial intracranial electrode array device wherein the interelectrode distance is between about 20 microns to about 2.5 mm in length.

One embodiment of the disclosure is directed to a transvenous electrical array device wherein the array materials soften or stiffen upon contact with neural tissue due to intrinsic properties of the polymer or allow, or due to external stimulation.

One embodiment of the disclosure is directed to a transvenous, transdural, or transarterial intracranial electrode array device further wherein the located between one or more, or proximal to the electrodes to enable multiplexing, wireless transmission, and wireless charge capabilities.

One embodiment of the disclosure is directed to a transvenous, transdural, or transarterial intracranial electrode array device wherein the lead extends from the electrode embedded substrate to a connector block.

One embodiment of the disclosure is directed to a transvenous, transdural, or transarterial intracranial electrode array device comprising implantable wireless transmission circuitry connected to the control circuitry and adapted to transmit digital data derived from the sensed brain electrical signals to receiving circuitry external to the site of device implantation.

One embodiment of the disclosure is directed to a transvenous, transdural, or transarterial intracranial electrode array device comprising implantable wireless receiver circuitry for receiving wireless commands transmitted from a site external to the site of device implantation, wherein the implantable control circuitry provides an electrical stimulus to the subject's brain via at least two of the brain-facing electrodes and records sensed electrical signals based on the reference voltage and the sensed electrical signals.

One embodiment of the disclosure is directed to a transvenous, transdural, or transarterial intracranial electrode array device comprising a transvenous and/or transdural anchor to prevent lead migration and/or to facilitate device retrieval.

One embodiment of the disclosure is directed to a transvenous, transdural, or transarterial intracranial electrode array device wherein the delivering the array occurs through introducing the array in a compressed state within a 2 mm or less in diameter or in a 3.14 cubic mm or less space within a hollow instrument.

One embodiment of the disclosure is directed to a transvenous, transdural, or transarterial intracranial electrode array device wherein the array is oriented in either planar or curvilinear configuration.

One embodiment of the disclosure is directed to a transvenous, transdural, or transarterial intracranial electrode array device wherein the external stimulation includes electrical, thermal, and magnetic stimuli.

One embodiment of the disclosure is directed to a method of placing a transvenous, transdural, or transarterial intracranial electrode array device comprising puncturing an extracranial vein percutaneously;

An embodiment of the disclosure is directed to a method of placing a transvenous, transdural, or transarterial intracranial electrode array device comprising creating a transvascular puncture site for advancement of a flexible hollow instrument with or without steerable properties; advancing a flexible hollow instrument with or without steerable properties to a site of intended implantation of the array within the intracranial vault; advancing the electrode array within the flexible hollow instrument; delivering an electrode array in a compressed state intravascularly through a flexible hollow instrument from the punctured extracranial vein to a desired implantation site located in the intracranial vault within subdural or subarachnoid space; and deploying the electrode array from the hollow instrument wherein the electrode array is deployed such that the electrode array expands once deployed from the hollow instrument and directly contacts a medium or tissue at an extravascular site within the intracranial vault.

One embodiment of the disclosure is directed to a method of placing a transvenous, transdural, or transarterial intracranial electrode array device comprising delivering the array intravascularly in a compressed state within a between about 0.5 mm to 2 mm diameter or in a 3.14 cubic mm or less space of a hollow instrument.

One embodiment of the disclosure is directed to a method of placing a transvenous, transdural, or transarterial intracranial electrode array device comprising microactuation of the array extravascularly in an expanded state between about 15 $cm^2$ to 125 $cm^2$ dimension within the subdural or subarachnoid space.

BRIEF DESCRIPTION OF THE DRAWINGS

Referring particularly to the drawings for the purpose of illustration only and not to limit the scope of the invention in any way, these illustrations follow.

DESCRIPTION OF THE EMBODIMENTS

Figure 1:
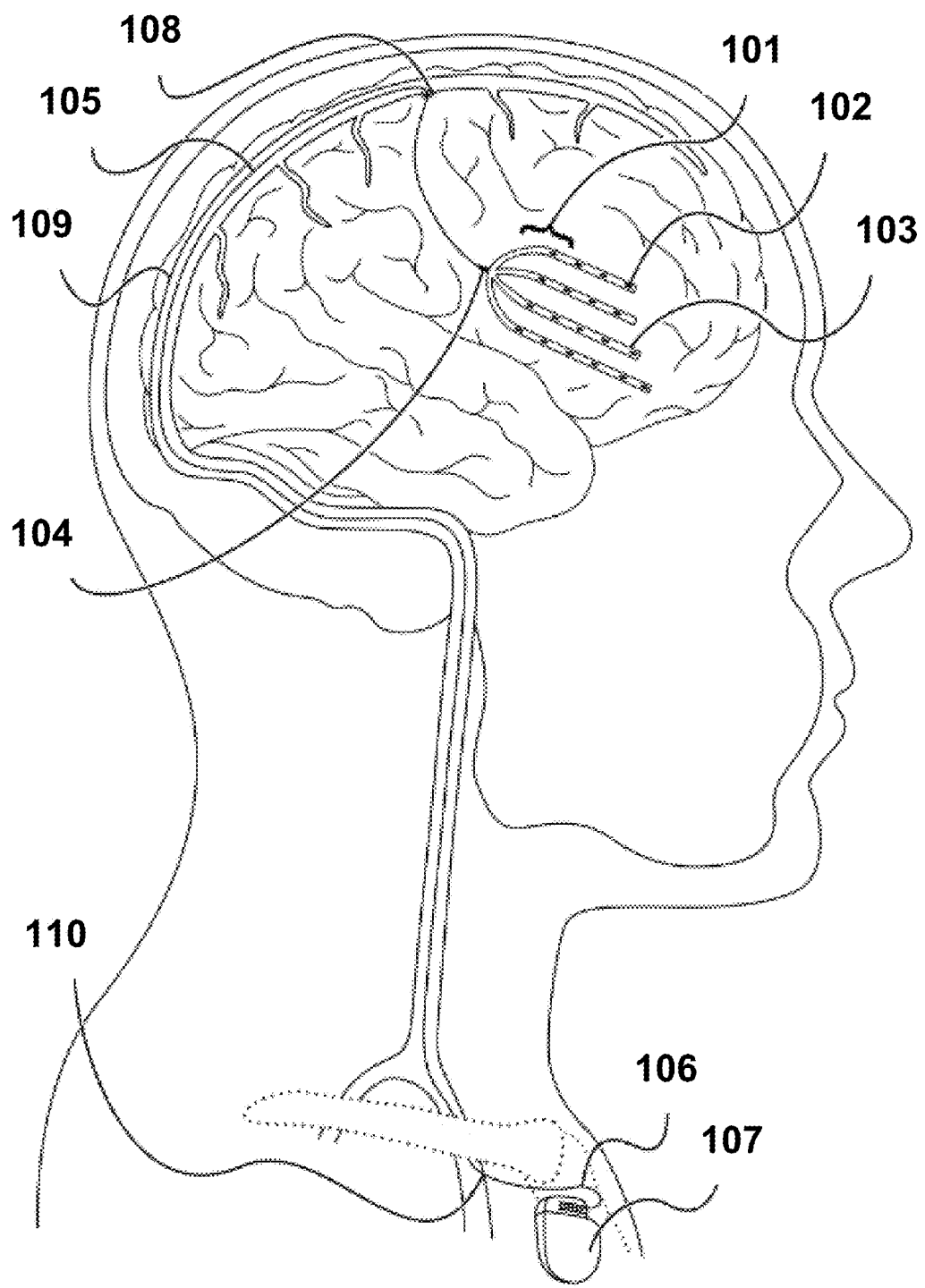
FIG. 1 is a diagram illustrating an embodiment of transvascularly introduced multipronged U-shaped electrode array device implanted intracranially.

Any discussion of documents, devices, acts, or knowledge in this specification is included to explain the context of the invention, and does not construe an admission that the disclosed innovation is not novel or that it does not represent a significant advancement above the current state of the art.

Unless otherwise defined, all technical terms used herein have the same meaning as commonly understood by one of ordinary skill in the art to which this disclosure belongs.

The articles "a" and "an" are used herein to refer to one or to more than one (i.e. at least one) of the grammatical object of the article. By way of example, reference to a "nucleic acid" means one or more nucleic acids.

The disclosed device is a spatially expansive electrode array comprised of one or more elongate members of substrate that may or may not be when two or more members are present. An electrode array embedded with a plurality of conductive materials. An electrode array scaffold compressible within a lumen of a flexible hollow delivery instrument for delivery through an endovascular route and expandable intracranially once released from the confines of said flexible hollow delivery instrument to occupy a volume or area in an extravascular neuroanatomical region of interest. A scaffold is meant to include: (a) a supporting substrate or framework that is superelastic, compressible, crimpable, flexible, or foldable for delivery; (b) a supporting substrate or framework that is either expandable, micro- or self-actuating once deployed from the confines of a flexible hollow delivery instrument. A substrate is meant to include a material that is either a liquid composite or a solid (e.g., polymer, alloy, and the like) and that is intrinsically self-actuating or coupled to an actuator (e.g., hydraulic or pneumatic), such as hydrogel, shape memory material (e.g., nitinol, microfluidic channel), and/or a thin-film (e.g., polyimide, polyurethane, silicone, parylene-C, NiTi, and the like) embedded with conductive materials.

A conductive material (e.g., platinum, gold, glassy carbon, iridium oxide, magnesium, silicon, nitinol, stainless steel, and the like) is meant to include functional elements, such as electrodes, traces, micro-wires, circuit components and the like, tailored for acute or chronic recording, measuring, stimulating, decoding or modulating of central nervous system media; an implantable substrate configured to having a cortical-facing side and an opposing side; a plurality of electrodes disposed on the cortical-facing side of the substrate and adapted for sensing, stimulating, decoding, or modulating electrical signals from a subject's brain; at least one reference conductive unit (i.e., electrode) mounted on the opposite side, wherein at least one reference electrode is physically separated from the subject's brain by the substrate and adapted to provide a reference voltage; optionally, a connector block configured to electrically couple the implanted device to an external device for processing, amplifying, acquiring, or transmitting detected signals; optionally, an implantable control circuit in communication with the cortical-facing electrodes and the opposing reference electrode; and optionally, a substrate embedded with one or more integrated circuits operably connected to one or more conductive materials for multiplexing, amplifying, processing, or transmitting acquired signals to enable decreased wire count and/or wireless telemetry.

Each elongate member or its independent members may be incorporated with a plurality of electrodes. The elongate members are delivered in a ≤3.14 cubic mm compressed state which is suitable for delivery within a flexible hollow or tubular delivery instrument (e.g., catheter, endoscope, or needle). The plurality of elongate members are comprised of flexible thin-film materials (e.g., polyimide, NiTi, parylene-C, or others known in the art) with intrinsic (i.e., shape memory materials/alloys (e.g., nitinol, NiTi thin film, chromium cobalt, or others known in the art) or hydroabsorbant materials) or extrinsic (i.e., microfluidic hydraulic channels) microactuating properties in 2-dimensional plane parallel to the topography of the cortical surface. Once deployed from this hollow or tubular instrument such as a catheter, needle, or endoscope, the device self-expands into a planar or curvilinear configuration, such that elongate members of the cortical array are arranged in parallel with the media or tissue plane.

Each member of the scaffold is comprised of an expandable shape memory or manipulated thin film substrate or subcarrier. The thickness of each member of the scaffold is thin enough to enable conformation to the contours of the media or tissue. The shape-memory alloy or polymer may be comprised of Nitinol, chromium-cobalt, thiol-ene, and/or hydrogel.

The shape-memory or self-expanding property may be conferred by intrinsic or externally applied actuators; other actuating mechanisms may include fluidic or pneumatic actuating channels, electro/magnetic responsive/active polymers, passive hydro-absorption, or more preferably by shape memory alloys, such as nitinol. The elongate members of the electrode array in an embodiment may be compressed, folded, or flexible enough to fit within the confines of a <3.14 cubic mm hollow instrument, such as a catheter, endoscope, or needle. An embodiment of the array is delivered intravascularly in a compressed state within the confines of a flexible hollow instrument, such as a catheter system, needle, or endoscope. After transvascular introduction and advancement, and subsequent deployment from the flexible hollow delivery instrument, the array is able to expand in the intracranial subdural or subarachnoid space for direct contact and interfacing with a large spatial area of media or tissue, for example 16 $cm^2$-125 $cm^2$.

An embodiment of the disclosure is comprised of a plurality of electrodes ranging size or diameter as small as 20 microns or as large as 1.5 mm. In one embodiment, small diameter microelectrodes are coated with at least one or a combination of superconductive materials including, but not limited to, iridium oxide, PEDOT:PSS, Niobium, and the like. This coating acts to minimize the electrical mismatch between the electrodes and the sensed or stimulated media or tissue. In another embodiment, the electrodes are not coated with superconductive materials. In another embodiment, some of the electrodes are coated with at least one superconductive material. The electrodes are spatially arranged so that the interspatial distance ranges from about 10 μm to about 1.5 mm. In one embodiment of the disclosure, larger electrodes, those ranging in size between 100 and 1000 μm are arranged so that there is an interspatial distance ranging between 1-10 mm. In another embodiment, smaller electrodes, those ranging in size between about 20 and 100 microns are arranged so that the array comprises an interspatial distance between the electrode ranging between about 50 and 500 microns. In another embodiment, there is a mixture of electrodes ranging in size between 20 and 1500 microns and these mixed sized electrodes are arranged so that there is an interspatial distance ranging between about 10 to 1500 microns. In all embodiments, the array is suitable for transport to its desired location through a hollow delivery instrument having an inner diameter of about 1-1.5 mm.

One embodiment of the array comprises an electrode end while the other end of the array is an adapter connector. The electrode end houses the electrodes. The electrode end is in contact with a wire bundle connector that is connected to a wire bundle. The wire bundle is then connected to the adapter connector. The adapter connector can be attached to an omnetic connector adapter for signal transmission.

One embodiment comprises transmitting signals through a wire to an analogue-to-digital converting and amplification circuit chip located on the array, elsewhere in the subject's body or in a remote location, such as a bedside module. In such an embodiment, signals may be processed with analogue-to-digital conversion and amplification on a circuit embedded on or near the array to improve signal resolution and enable channel multiplexing, which decreases wire bundle size. Such an embedded circuit enables low energy consumption, amplification, and high signal to noise ratio transmission via wire or wireless transmission.

FIG. 1 illustrates an embodiment of the disclosure wherein the embodiment of the transvascularly introduced multipronged U-shaped electrode array 101 device is implanted intracranially. In this embodiment, the electrode array 101 is anchored 108 across a dural encased sinus 109, and a lead 105 within a vein exiting subclavicularly 110 and connecting 106 to a subcutaneous connector block implant 107. The subcutaneous connector block implant 107 comprises at least one battery, ADC, integrated circuit, clock, amplifier, and/or programmable chip. The array 101 comprises at least one connector to wire bundle 104, at least one scaffold/thin film elongate member 103, and at least one electrode or sensor 102.

Figure 2:
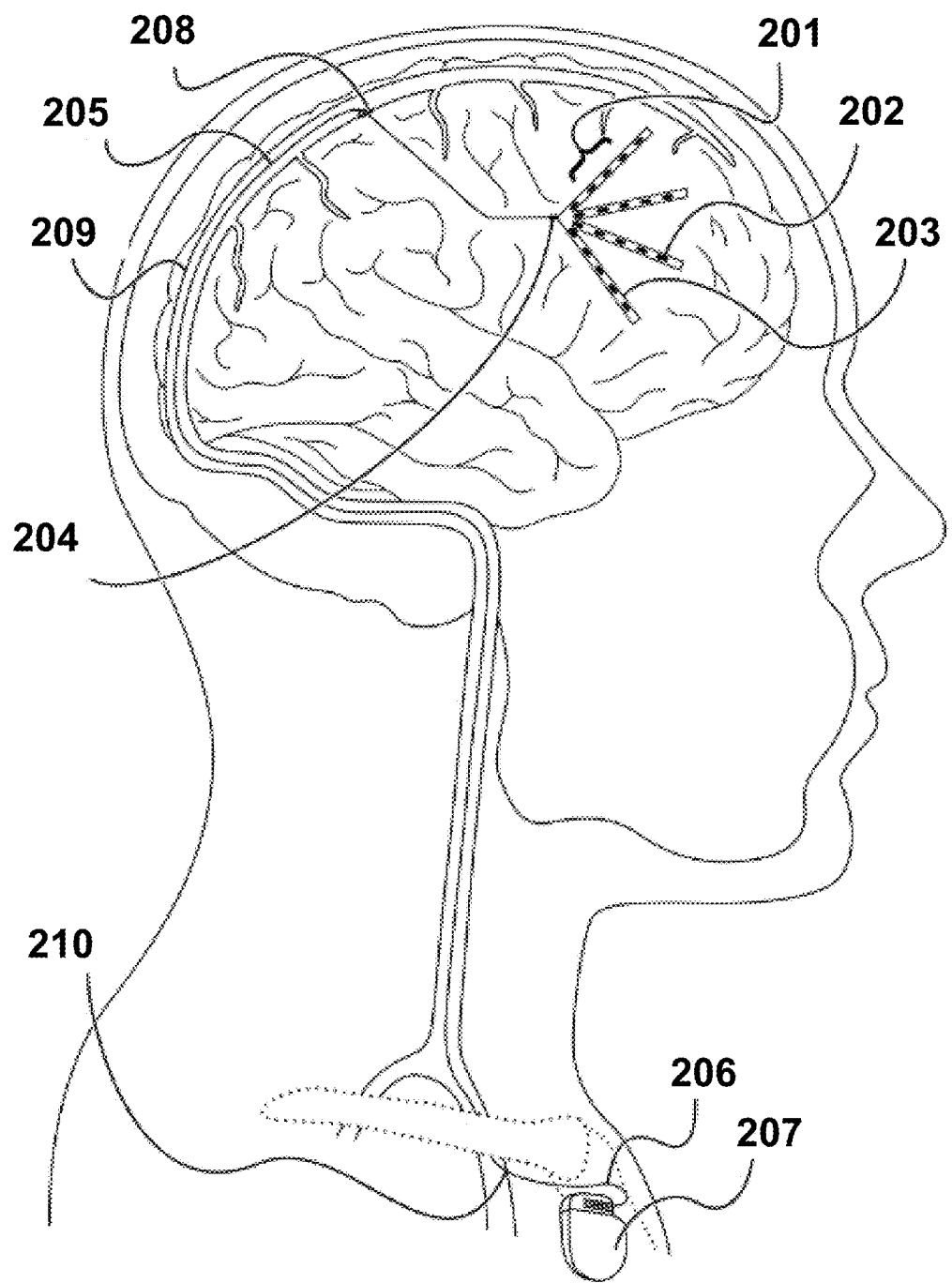
FIG. 2 is a diagram illustrating an embodiment of transvascularly introduced multipronged planar radial shaped electrode array device implanted intracranially, anchored across a dural encased sinus, and transvenous leads exiting subclavicularly to a subcutaneous connector block implant.

FIG. 2 is a diagram illustrating an embodiment of transvascularly introduced multipronged planar radial shaped electrode array 201 device implanted intracranially, anchored 208 across a dural encased sinus 209, and transvenous leads 205 exiting subclavicularly 210 and connecting through a connector 206 to a subcutaneous connector block implant 207. The array 201 comprises at least one connector to wire bundle 204, at least one scaffold/thin film elongate member 203, and at least one electrode or sensor 202.

Figure 3:
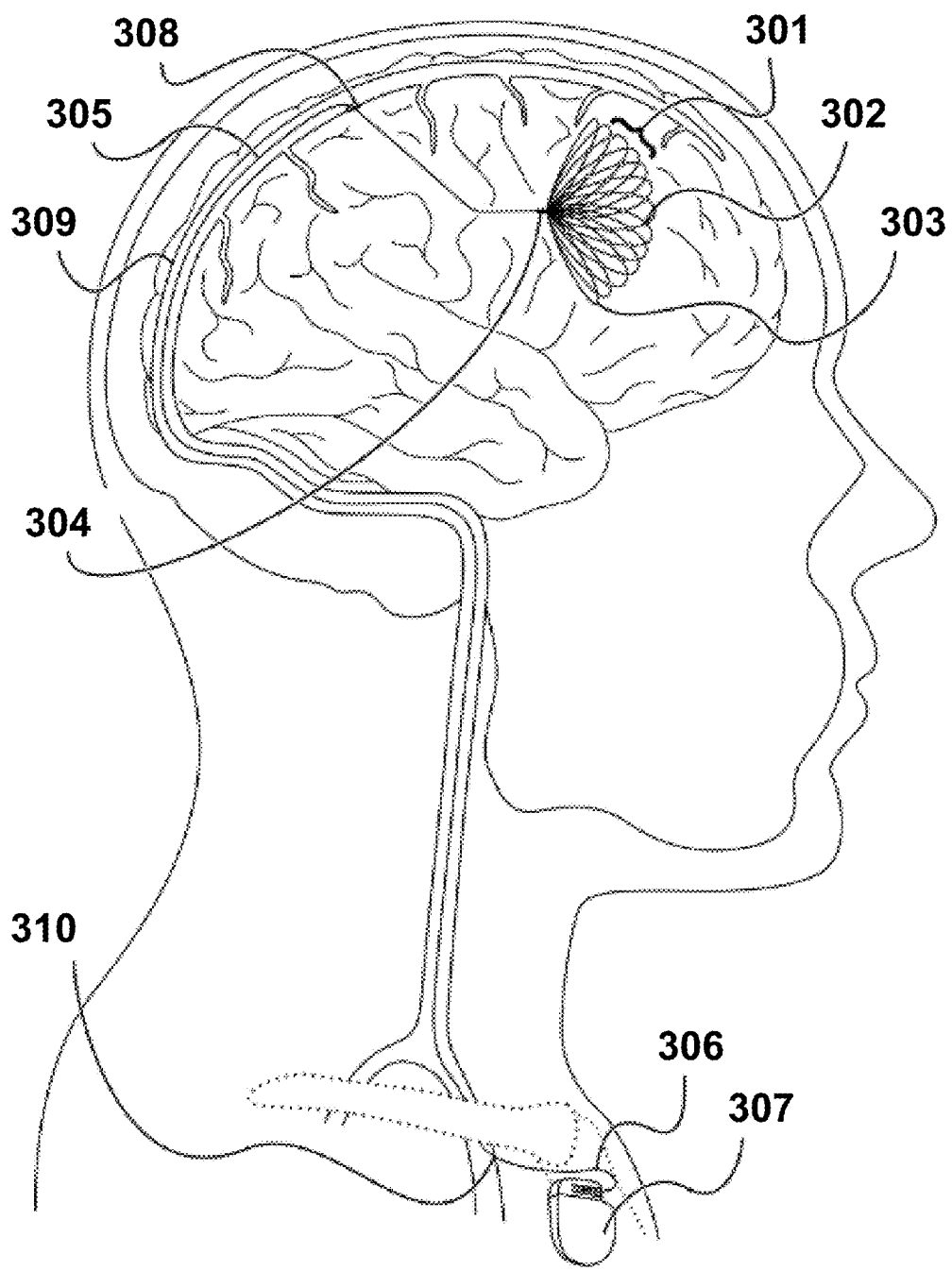
FIG. 3 is a diagram illustrating an embodiment of transvascularly introduced wire-formed multipronged loop electrode array device implanted intracranially, anchored across a dural encased sinus and leads exiting subclavicularly to a subcutaneous connector block implant.

FIG. 3 is a diagram illustrating an embodiment of transvascularly introduced wire-formed multipronged loop electrode array 301 device implanted intracranially, anchored 308 across a dural encased sinus 309 and leads 305 exiting subclavicularly 310 connecting through a connector 306 to a subcutaneous connector block implant 307. In such an embodiment, the wire-formed multipronged loop electrode array 301 comprises at least one wire scaffold 303 and at least one electrode or sensor 302. In some embodiments, the array 301 comprises at least one connector to wire bundle 304 and/or adaptor.

Figure 4:
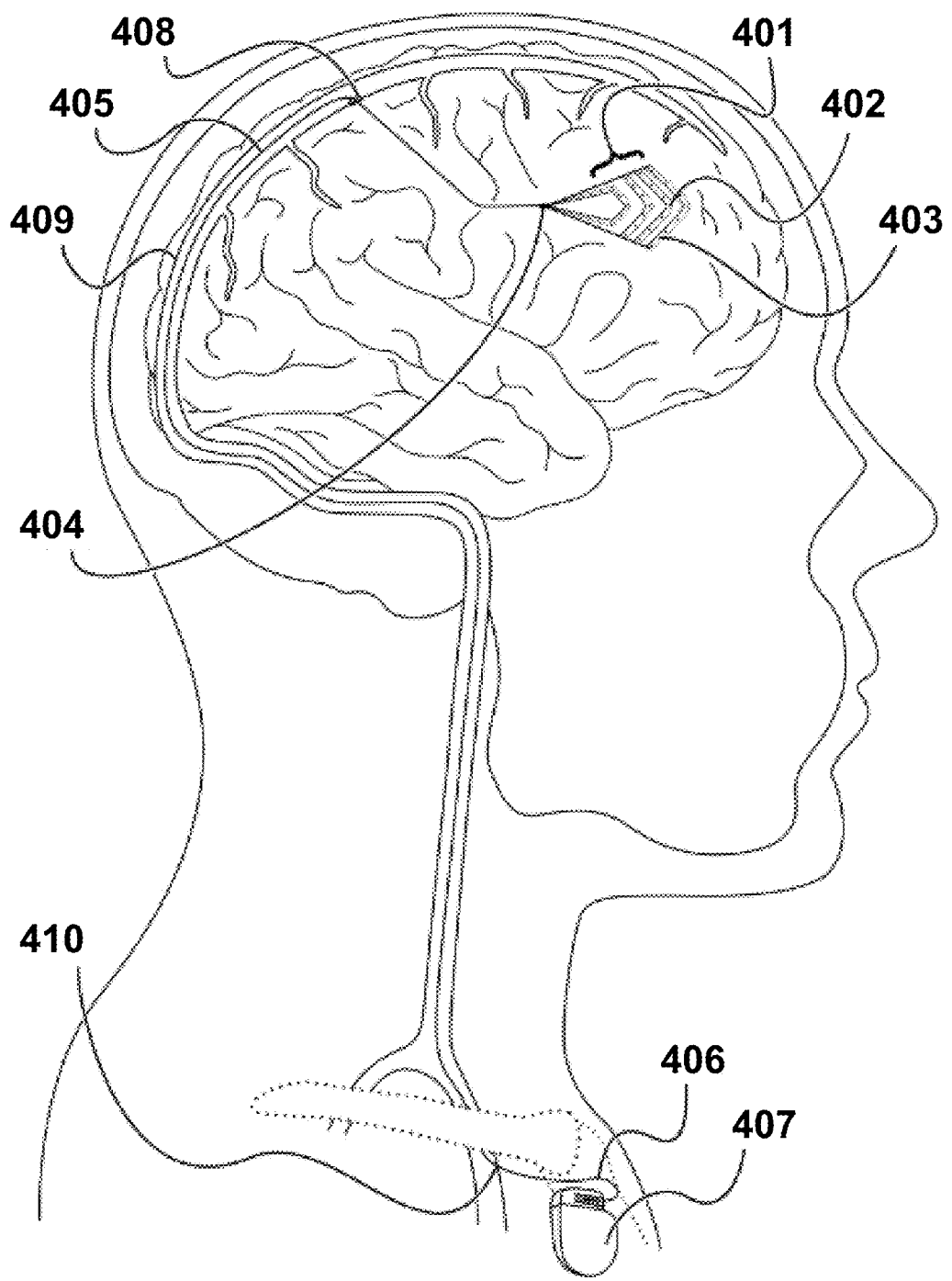
FIG. 4 is a diagram illustrating an embodiment of transvascularly introduced shape-within-shape pentagon electrode array device implanted intracranially, anchored across a dural encased sinus, and transvenous leads exiting subclavicularly to a subcutaneous connector block implant.

FIG. 4 is a diagram illustrating an embodiment of transvascularly introduced shape-within-shape pentagon electrode array 401 device implanted intracranially, anchored 408 across a dural encased sinus 409, and transvenous leads 405 exiting subclavicularly 410 through a connector 406 to a subcutaneous connector block implant 407. The shape-within-shape pentagon electrode array 401 comprises at least one scaffold 403 and at least one electrode or sensor 402. The shape within a shape electrode array 401 can be of any shape and does not have to be a pentagon. For example, a circle, triangle, oval, parallelogram, rectangle, or any other two-dimensional shape can be used as will cover the required brain area to be measured, recorded, stimulated, decoded, modulated, and/or monitored. The array 501 comprises at least one connector to wire bundle 504 and/or adaptor.

Figure 5:
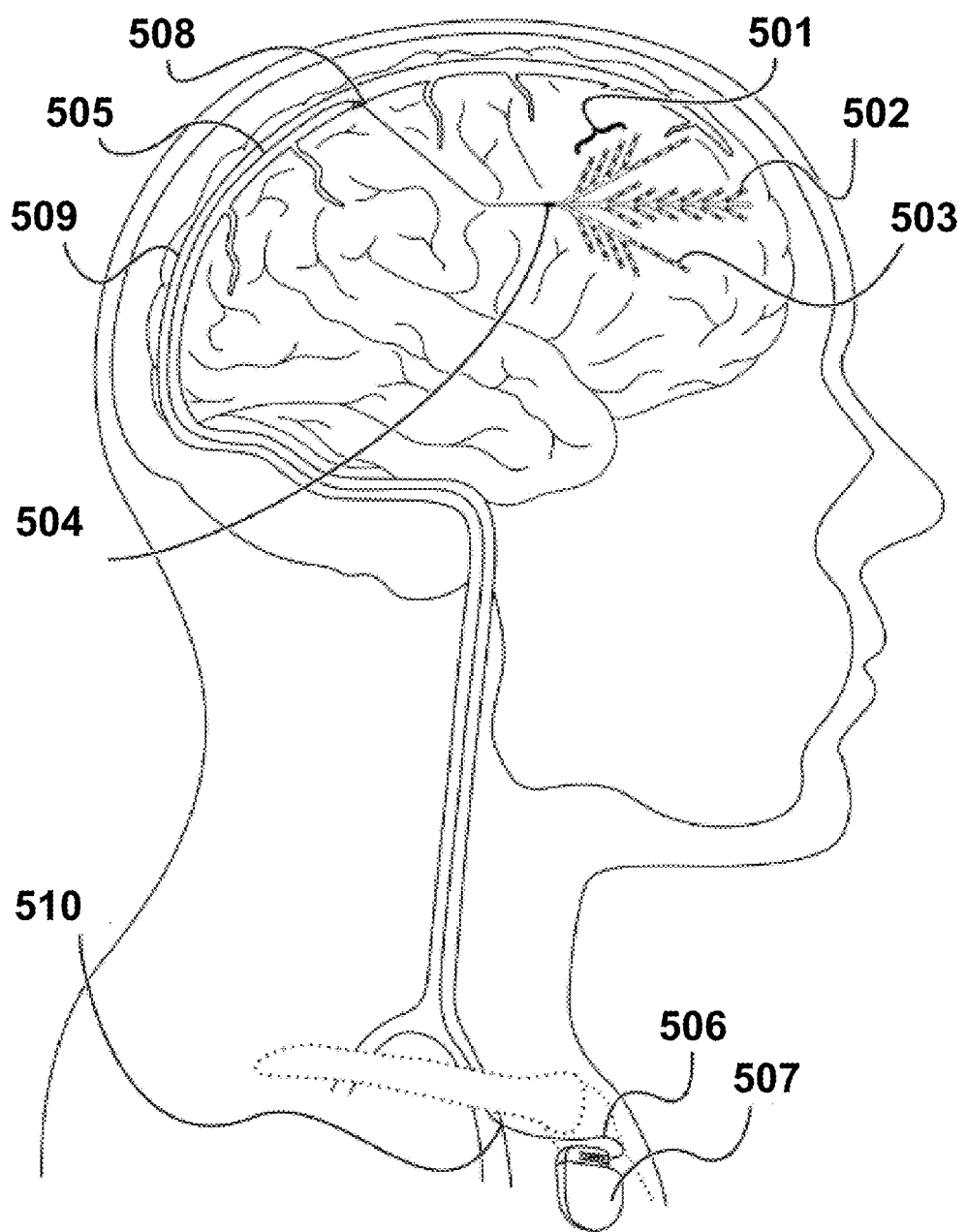
FIG. 5 is a diagram illustrating an embodiment of transvascularly introduced fractal-like branching electrode array device implanted intracranially, anchored across a dural encased sinus, and transvenous leads exiting subclavicularly to a subcutaneous connector block implant.

FIG. 5 is a diagram illustrating an embodiment of a transvascularly introduced fractal-like branching electrode array device 501 implanted intracranially, anchored 508 across a dural encased sinus 509, and transvenous leads 505 exiting subclavicularly 510 through a connector 506 to a subcutaneous connector block implant 507. In such an embodiment, the fractal-like branching electrode array 501 comprises at least one branching scaffold 503 and at least one electrode or sensor 502. In some embodiments, the array 501 comprises at least one connector to wire bundle and/or adaptor 504.

Figure 6:
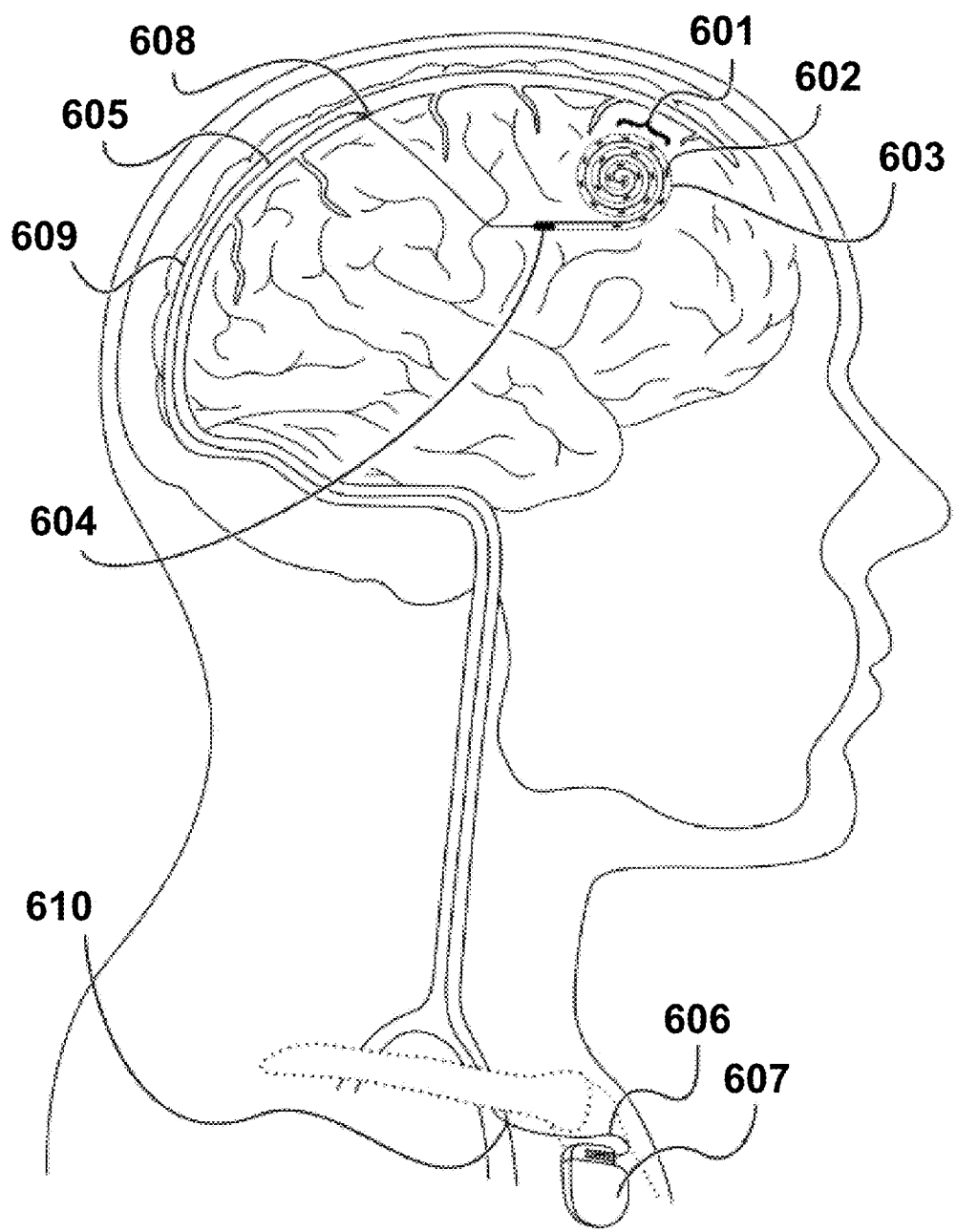
FIG. 6 is a diagram illustrating an embodiment of transvascularly introduced concentric electrode array device implanted intracranially, anchored across a dural encased sinus, and transvenous leads coursing within intracranial venous channels.

FIG. 6 is a diagram illustrating an embodiment of transvascularly introduced concentric electrode array 601 device implanted intracranially, anchored 608 across a dural encased sinus 609, and transvenous leads 605 coursing within intracranial venous channels and exiting subclavicularly 610 through a connector 606 to a subcutaneous connector block implant 607. at least one connector to wire bundle 604, at least concentric elongate member 603, and at least one electrode or sensor 602.

Figure 7:
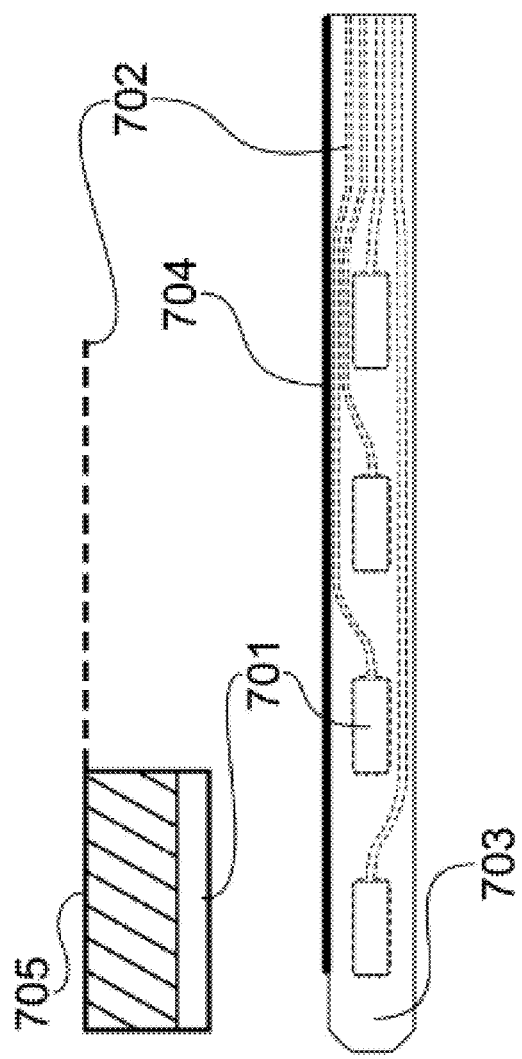
FIG. 7 is a diagram illustrating an embodiment of a singular thin-film substrate member of an array embedded with a plurality of electrodes, an electrode backing layer, and conductive traces.

FIG. 7 illustrates an embodiment of the disclosure comprising a singular thin-film substrate member of an array embedded with a plurality of electrodes 701, an electrode backing layer 705, and conductive traces 702. The embodiment of the singular film substrate member comprises a scaffold member 703 and an SMA actuator 704.

Figure 8:
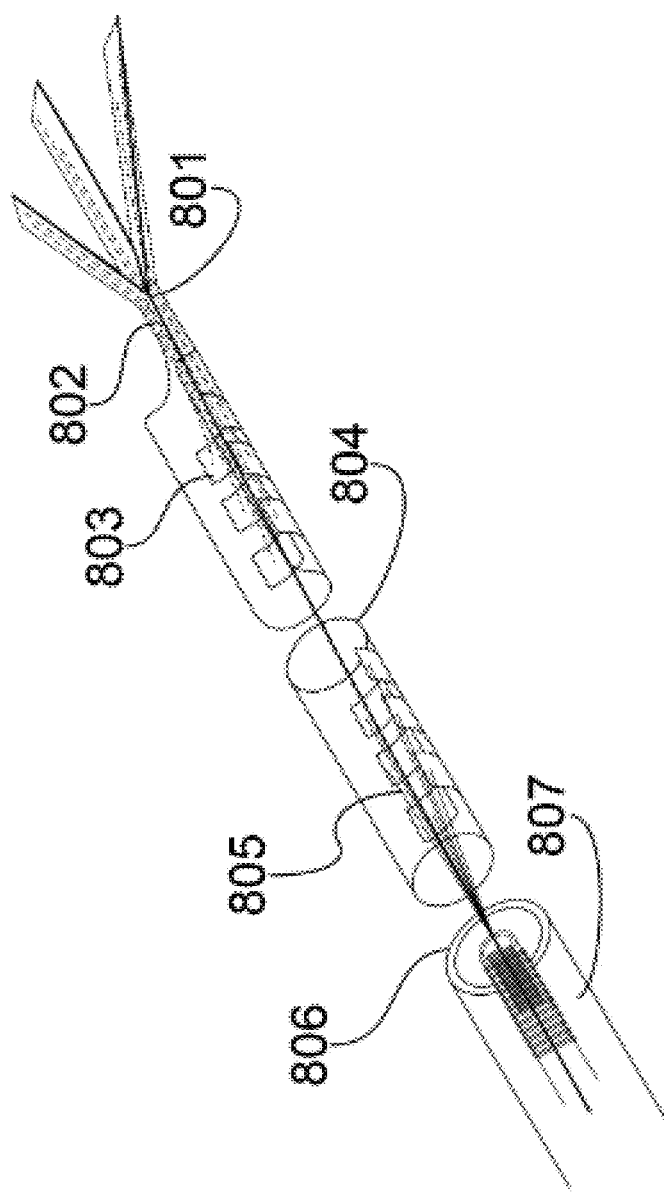
FIG. 8 is a diagram illustrating an embodiment of the proximal extent of an electrode array, the shape memory actuators, an intermediary flexible printed circuit board and/or wire bundle connector, and microwires or leads wrapped around a shaft forming a wire bundle or an extension cable for wired signal transmission.

FIG. 8 is a diagram illustrating an embodiment of the proximal extent of an electrode array, the shape memory actuators 802, an intermediary flexible printed circuit board and/or wire bundle connector 801, and microwires or leads 805 wrapped around a shaft forming a wire bundle or an extension cable for wired signal transmission.

Figure 9:
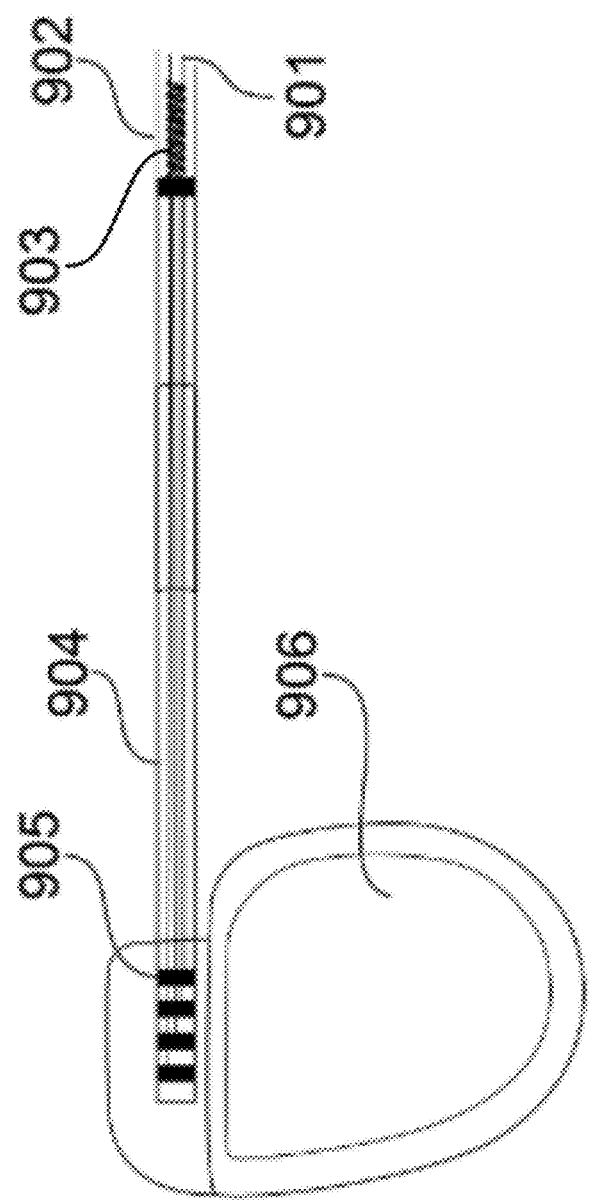
FIG. 9 is a diagram illustrating the extension cable inserted into a subcutaneously implantable control unit.

FIG. 9 is a diagram illustrating the extension cable inserted into a subcutaneously implantable control unit where the control unit comprises a stylet 901, a hypotube 902, at least one helically wound microwire 903, an insulated lead 904, a connector 905, and a connector block 906.

Figure 10A:
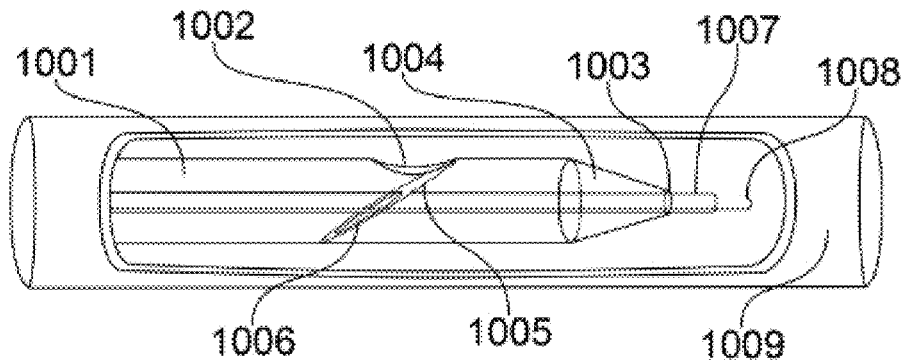
FIGS. 10A-10H illustrate a sequence of process steps for performing transvascular access procedure to access extravascular spaces within the intracranial vault with a catheter, delivery of the array in a collapsible state through catheter situated extravascularly, and deployment of the array for implantation in the intracranial subdural or subarachnoid space.
Figure 10B:
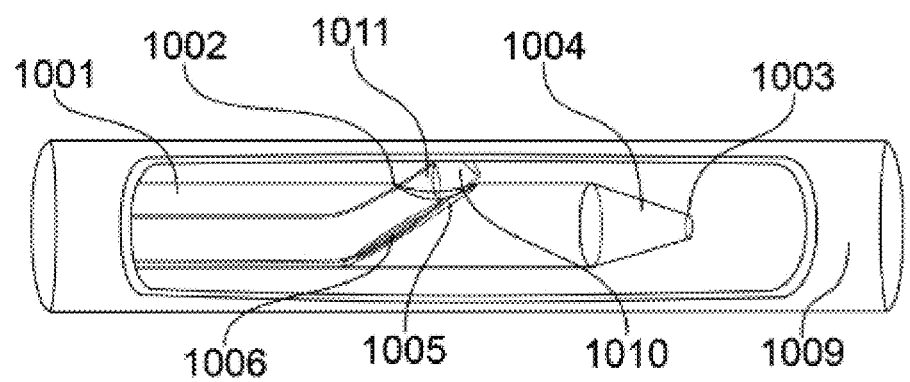
Figure 10C:
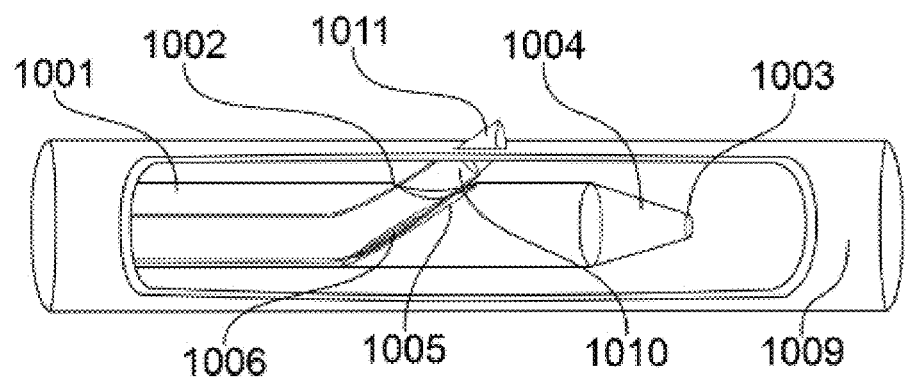
Figure 10D:
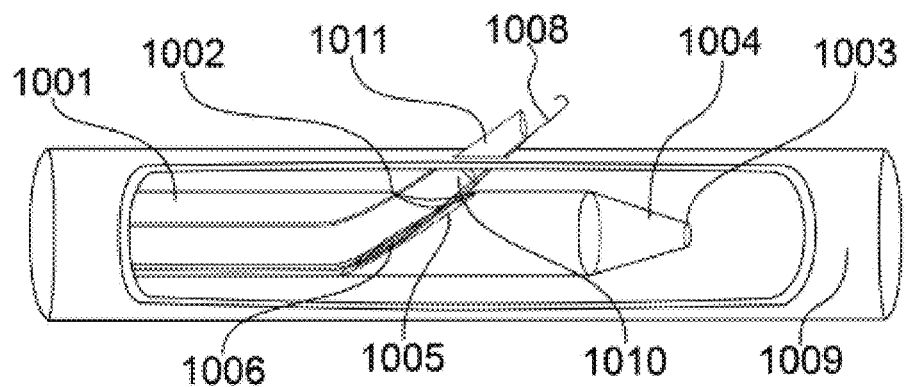
Figure 10E:
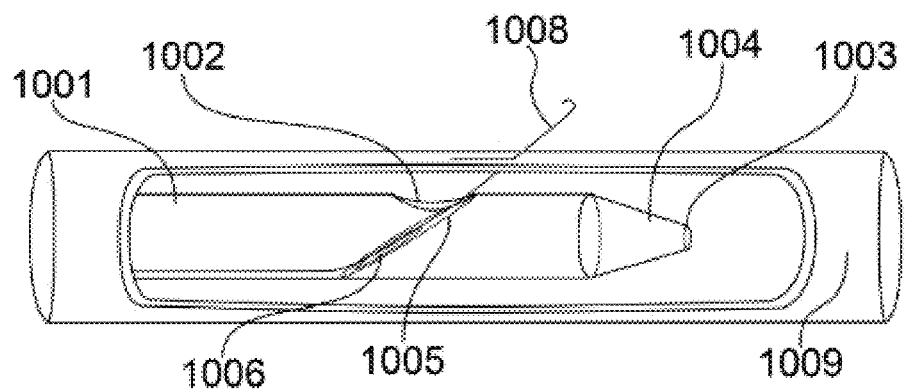
Figure 10F:
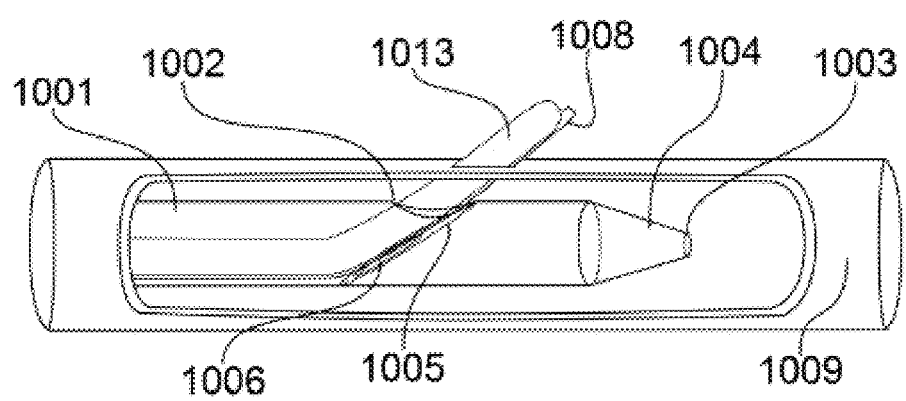
Figure 10G:
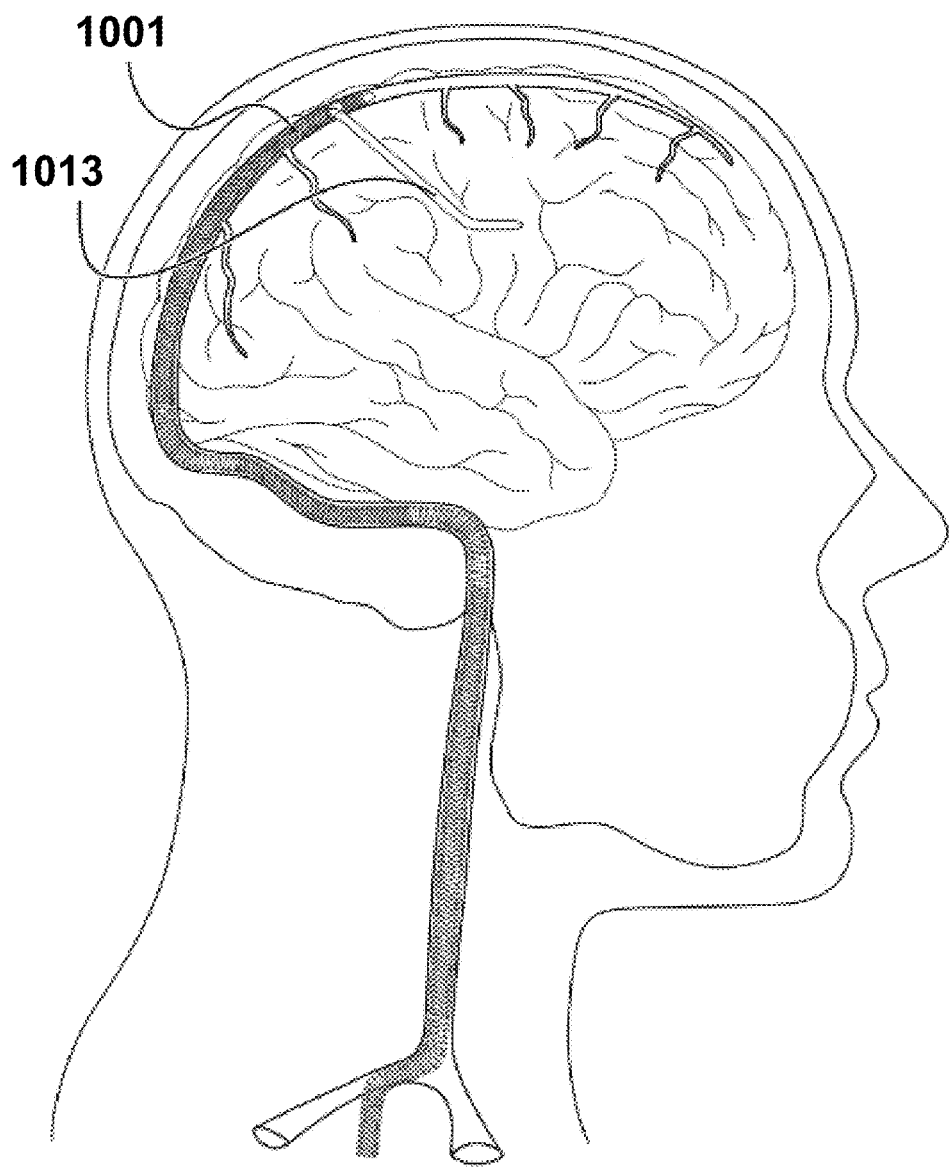
Figure 10H:
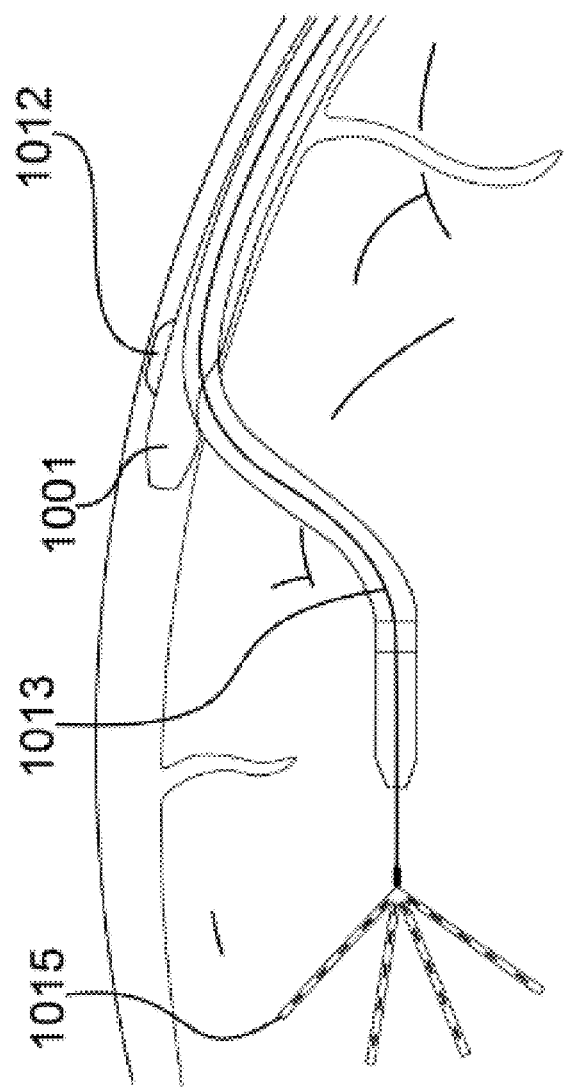

FIGS. 10A through 10H illustrate a sequence of process steps for performing a transvascular access procedure to access extravascular spaces within the intracranial vault with a catheter 1013 (FIG. 10F), delivery of an array 1015 in a collapsible state (FIG. 10H) through a catheter 1011 situated extravascularly, and deployment of the array 1015 for implantation in the intracranial, subdural, or subarachnoid space (FIG. 10H). FIG. 10A illustrates cerebral venous access using a microguidewire 1008 and microcatheter 1011 coaxially advanced through a selective passageway and deployed from the distal end working exit port 1003 of a guide/access catheter 1001. The guide/access catheter 1001 may have a tapered tip 1004. In a first step an endovascular guide/access catheter 1001 may be positioned within a cerebral vein 1009 using a 0.014 or 0.018 inch microguidewire 1008, coaxially introduced through a microcatheter 1007, which may feature built-in pull-wires for steerable capabilities, together in a telescoped configuration. The endovascular guide/access catheter 1001 may include a side exit port or a lateral working lumen exit port 1002 and a distal working lumen exit port 1003. The endovascular guide/access catheter 1001 may also include a selective deflector 1005 with luminal molding 1006. Inflation or expansion of a compliant structure 1012 (bonded balloon(s)

or wire mesh structural members(s)) may also be used to maintain the position of the lateral working exit lumen port near/against the endoluminal surface of the vein at an entry point of interest. Additionally, inflation or expansion of the same compliant structure(s) (e.g., balloon(s) or wire mesh structural member(s)) may also be used to provide a buffer against the back propagation of forward insertion forces.

FIG. 10B illustrates removal of the microcatheter 1007 and microguidewire 1008 from the guide/access catheter 1001 shaft lumen.

FIG. 10C illustrates co-axial introduction and deployment of a catheter or related instrumentation 1011 through the lateral wall working exit lumen port 1002. A retractable needle sheath 1010 may facilitate needle delivery without damaging the inner liner as it is co-axially delivered within the main catheter lumen through tortuous venous anatomy.

FIG. 10D illustrates transvenous and/or transdural puncture with a penetrating member across the vessel wall and into the brain parenchyma, subdural or subarachnoid space. In some embodiments, the vessel, and if applicable, the encasing dura, may be punctured with a penetrating catheter or needle from the lateral wall working exit lumen port 1002 into a perivascular space.

FIG. 10E illustrates transvascular advancement and placement of a guidewire 1008 through the penetrating member into the brain parenchyma, subdural and/or subarachnoid space to guide subsequently introduced co-axial catheters or instrumentation. The guidewire 1008 may then be advanced through the penetrating catheter or needle with the guidewire 1008 placed across the venous puncture site. A dilating catheter may be co-axially introduced via over the wire techniques through a flexible, 'soft' tip catheter deployed from the lateral wall working lumen exit port 1002 across the venous puncture site and into the subdural space. The subdural space may be navigated with a flexible, 'soft' tip catheter equipped with remote stability control.

The methods described herein may be used for the transcatheter deployment or delivery of a flexible brain biopsyneedle, a single or a multi-mode optical fiber for in situ imaging or a laser interstitial thermal therapy, respectively, a self-expandable electrode array, or an implantable nanofluidic apparatus. These transcatheter devices or implants and the methods described herein may be used to diagnose, treat, or investigate intracranial tissue or media in an anatomical boundary of interest located a distance (i.e., centimeters) from the transvascular puncture site. Catheters or transcatheter instruments may facilitate implantation, anchoring, or retrieval of a device. During or after the transvascular procedure, a balloon member located near, at, or beyond the distal end of the catheter may be deflated to allow for rotational or axial positioning of the endovascular catheter with the punctured vein. An elastomeric compliant or ultra-compliant balloon member may then be inflated over the transvascular puncture site to seal or tamponade the vascular wall defect. In some instances, a bioreabsorbable hemostatic material may be deployed over the transvascular access site to achieve hemostasis.

The guide/access catheter 1001 may be positioned within the vein 1009 using a guide catheter co-axially introduced over a guidewire and advanced through a selective passageway (<0.87 mm) and deployed from the distal end working exit lumen port 1003 of the guide/access catheter 1001. The microcatheter 1007 and guidewire 1008 may be retracted from the central lumen of the guide/access catheter 1001. In some embodiments, a flexible access needle may be co-axially introduced into the central lumen of the guide/access catheter 1001. In the next step, a compliant structure (or structures) is (are) expanded, positioning the lateral wall working lumen exit port 1002 against the intended venous access site. In the next step, a flexible needle coated with polymeric material (e.g., polytetrafluoroethylene, etc.) and/or sheathed in a retractable guard or catheter may be selectively deployed out of the lateral wall working exit lumen port 1002. In the next step, the flexible needle penetrates transmurally across the vessel wall being reinforced with a stylet for tensile strength. After puncturing across the vein, the stylet is withdrawn and a guidewire is advanced co-axially through the unreinforced flexible needle, such that it abuts the encasing dural layer. The flexible needle is withdrawn leaving the guidewire in place across the venous puncture site and abutting the encasing dura as a placeholder.

An embodiment of the disclosed device comprises two sides, a cortical facing side and a dura facing side. The cortical facing side is the side which faces and comes in contact with brain tissue. The cortical facing side comprises a plurality of electrodes that are used to stimulate, sense, and record electrical signals to/from a patient's brain.

The dura facing side of the device, located opposite to the cortical facing side, is the side facing the outer most membrane enveloping the brain. The dura facing side comprises at least one reference electrode. The reference electrode is physically separated from the subject's brain by the flexible substrate and provides a reference voltage.

In one embodiment of the disclosure, the array comprises an electrode end and a wireless connector end where the wireless connector end is used to wirelessly transmit signals to and from the array by way of a wireless transmitter. The array transmits signals wirelessly to or receives wirelessly transmitted signals from a nearby module from a remotely located/implanted or embedded chip. In such an embodiment, the array is leadless and wirelessly transmitted. In such an embodiment, the wireless communications are any wireless communication known in the art, in particular, radiofrequency (RF), ultrasound, or wideband. In one embodiment, the array comprises at least one antenna and at least one transceiver on the internal and external portion of the array.

An embodiment of the disclosure comprises a transvenous and/or transdural anchor. The anchors secure the device in place. This prevents lead migration but can also aide in device retrieval. In one embodiment the array is retrievable requiring only a minutely invasive procedure. In one embodiment the array does not require retrieval. In one embodiment, the array can remain in its deposited location. In yet another embodiment, the array is degradable with the use of specific materials (e.g., silk, magnesium, silicon, cellulose, etc.).

An embodiment of the current disclosure is the implantation of a disclosed spatially expansive electrode array through intravascular travel where the array is in a compressed state and within the confines of a hollow delivery instrument. The spatially expansive electrode array is configured for extravascular navigation within the intracranial vault, comprising a neural interfacing microactuating array delivered via a transvascular procedure catheter dimensioned to be launched out of the side exit port by the selective deflector configured to deliver the microactuating array in the intracranial subdural or subarachnoid space for direct contact with the tissue or fluid media; and interfacing with a large spatial area of media or tissue After the extravascular deployment of the array from the hollow delivery instrument of a transvascular access system, the array expands, unfurls/unfurls to its planar or curvilinear three-dimensional shape.

What is claimed is:

1. An electrode array device for detecting, measuring, recording, stimulating, decoding, mapping, and/or modulating brain activity at a site of device implantation, comprising:
    a scaffold comprising one or more substrate members, the one or more substrate members embedded with conductive materials;
    an external device in electrical communication with the conductive materials; and
    a flexible hollow delivery instrument configured to translate the scaffold and its one or more substrate members from a transvascular access site in a vessel to a target extravascular location within the intracranial vault of a patient; wherein:
        the scaffold and its one or substrate members are configured to be confined to a small volume for containment in the flexible hollow delivery instrument during translation through the transvascular access site to the target extravascular location within the intracranial vault;
        the external device and the conductive materials are configured for the transfer of electrical signals between the target extravascular location within the intracranial vault and the external device;
        the flexible hollow delivery instrument is further configured to translate the one or more substrate members through a puncture at the transvascular access site, out of the vessel, and to the target extravascular location within the intracranial vault;
        the one or more substrate members are further configured to be deployed to the target extravascular location within the intracranial vault; and
        the one or more substrate members are further configured to expand over a selected area of the patient's brain such that the conductive materials electrically couple with neural tissue of the patient's brain.

2. The device of claim 1, wherein the external device and the conductive materials are further configured to enable one or more activity selected from the list consisting of: mapping of cortical activity, stimulation of neurons, and modulation of interfacing neural activity.

3. The device of claim 1, wherein the conductive materials comprise wires traversing the length of a shaft of the scaffold.

4. The device of claim 3, wherein the wires are connected to the external device by a connector block.

5. The device of claim 1, further comprising implantable wireless receiver circuitry configured to enable wireless communication with the external device.

6. The device of claim 1, further comprising a catheter configured to be coupled to the one or more substrate members and to remain coupled to the one or more substrate members after their deployment, and configured to retract the one or more substrate members into the catheter for removal after the transfer of electrical signals is complete.

7. The device of claim 6, wherein the catheter is configured to decouple from the one or more substrate members, and to be removable from the patient after deployment of the one or more substrate members, such that the one or more substrate members remain electrically coupled with the neural tissue of the patient's brain.

8. The device of claim 1, wherein each one of the one or more substrate members comprises a dura-facing side and an opposing cortex-facing side.

9. The device of claim 8, wherein the dura-facing side comprises at least one reference electrode that is configured to be electrically separated from the brain, and wherein the at least one reference electrode is configured to provide a reference voltage.

10. The device of claim 1, wherein the one or more substrate members comprise one or more component selected from the list consisting of: an integrated circuit, a microbattery, and an RF antenna.

11. The device of claim 1, wherein the one or more substrate members further comprise an integrated circuit, the integrated circuit configured to perform one or more task selected from the list consisting of: signal conditioning, amplification, filtering, analog-to-digital conversion, stimulus amplification, and stimulus waveshaping.

12. The device of claim 1, further comprising an outer catheter comprising a distal end comprising a side exit port and a deflecting member, wherein the deflecting member is configured to deflect a puncture tool through the side exit port when pushed, to thus puncture the vessel when the outer catheter resides therein, and wherein the deflecting member is configured to deflect the one or more substrate members in a compressed state through the side exit port and through the puncture in the vessel allowing for deployment of the one or more substrate members.

13. The device of claim 12, wherein the puncture tool comprises a first inner catheter and wherein the one or more substrate members in the compressed state comprise a second inner catheter, the first and second inner catheters configured to be placed sequentially in the outer catheter.

14. The device of claim 1, wherein the one or more substrate members comprise one or more item selected from the list consisting of: a compressible sheet of material, a rigid material with elongated elements that are configured to fan out when deployed, and a combination of a rigid material and a compressible sheet of material.

15. The device of claim 1, wherein the one or more substrate members comprise a plurality of elongate members comprising flexible thin-film material having intrinsic or extrinsic microactuating properties.

16. The device of claim 15, wherein the flexible thin-film material comprises one of more material selected from the list consisting of: a shape memory material, a hydroabsorbant material, a microfluidic, a pneumatic, and a hydraulic channel.

17. The device of claim 1, wherein the one or more substrate members form a two-dimensional surface to cover the selected area of the patient's brain.

18. The device of claim 1, wherein the one or more substrate members comprise a three dimensional surface formed of elongate members or a balloon.

19. The device of claim 1, wherein the scaffold comprises:
    a supporting substrate or framework wherein the substrate or framework comprises at least one superelastic, compressible, crimpable, flexible, or foldable material configured to be expandable, microactuating, or self-actuating after deployment from the flexible hollow delivery instrument.

20. The device of claim 1, further comprising a transvenous and/or transdural anchor configured to prevent migration of the scaffold.

* * * * *